(12) United States Patent
Hoyle

(10) Patent No.: US 7,202,774 B2
(45) Date of Patent: Apr. 10, 2007

(54) EYE SHIELD SLEEPING DEVICE

(76) Inventor: Reginald E. Hoyle, 112 Schenck Farm Rd., Lawndale, NC (US) 28090

( * ) Notice: Subject to any disclaimer, the term of this patent is extended or adjusted under 35 U.S.C. 154(b) by 96 days.

(21) Appl. No.: 10/929,929

(22) Filed: Aug. 28, 2004

(65) Prior Publication Data

US 2005/0046549 A1 Mar. 3, 2005

Related U.S. Application Data

(63) Continuation-in-part of application No. 29/207,843, filed on Jun. 18, 2004, which is a continuation-in-part of application No. 29/188,431, filed on Aug. 19, 2003, now Pat. No. Des. 492,955.

(51) Int. Cl.
*G08B 1/00* (2006.01)
(52) U.S. Cl. .............. 340/309.16; 340/693.9; 340/573.1; 368/244; 381/23.1; 2/6.7
(58) Field of Classification Search .......... 340/309.16, 340/573.1, 693.5, 693.9; 368/244, 10; 381/23.1, 381/312; 2/15
See application file for complete search history.

(56) References Cited

U.S. PATENT DOCUMENTS

D485,854 S * 1/2004 Thomason ................ D16/301
6,961,286 B1 * 11/2005 Alagia ........................ 368/10
2004/0188229 A1 * 9/2004 Ullmann et al. ......... 200/43.16
2006/0044143 A1 * 3/2006 Randolph ................ 340/573.5

FOREIGN PATENT DOCUMENTS

JP 404155290 A * 5/1990

* cited by examiner

*Primary Examiner*—Jeffery Hofsass
*Assistant Examiner*—Hongmin Fan
(74) *Attorney, Agent, or Firm*—Clements Walker; F. Rhett Brockington

(57) ABSTRACT

The invention is an eye shield sleeping device that has a strap, a pair of eye shields, a pair of ear covers, a timer, one or more speakers, a microphone, and a voice recognition system. The timer creates an awakening sound when the time on the timer expires. The sound is produced by the speaker mounted inside the ear cover. The user can control the device using commands issued to the voice recognition system. The device can be connected to a media and communication appliance, such as a cell phone, a computer, and a digital player, which can play through the speakers. The voice recognition system can also be used to control a connected appliance. The principal function of the device is to create a restful environment for the user for a controlled period of time. Anticipated applications include naps while traveling and in sleep rooms at work.

23 Claims, 3 Drawing Sheets

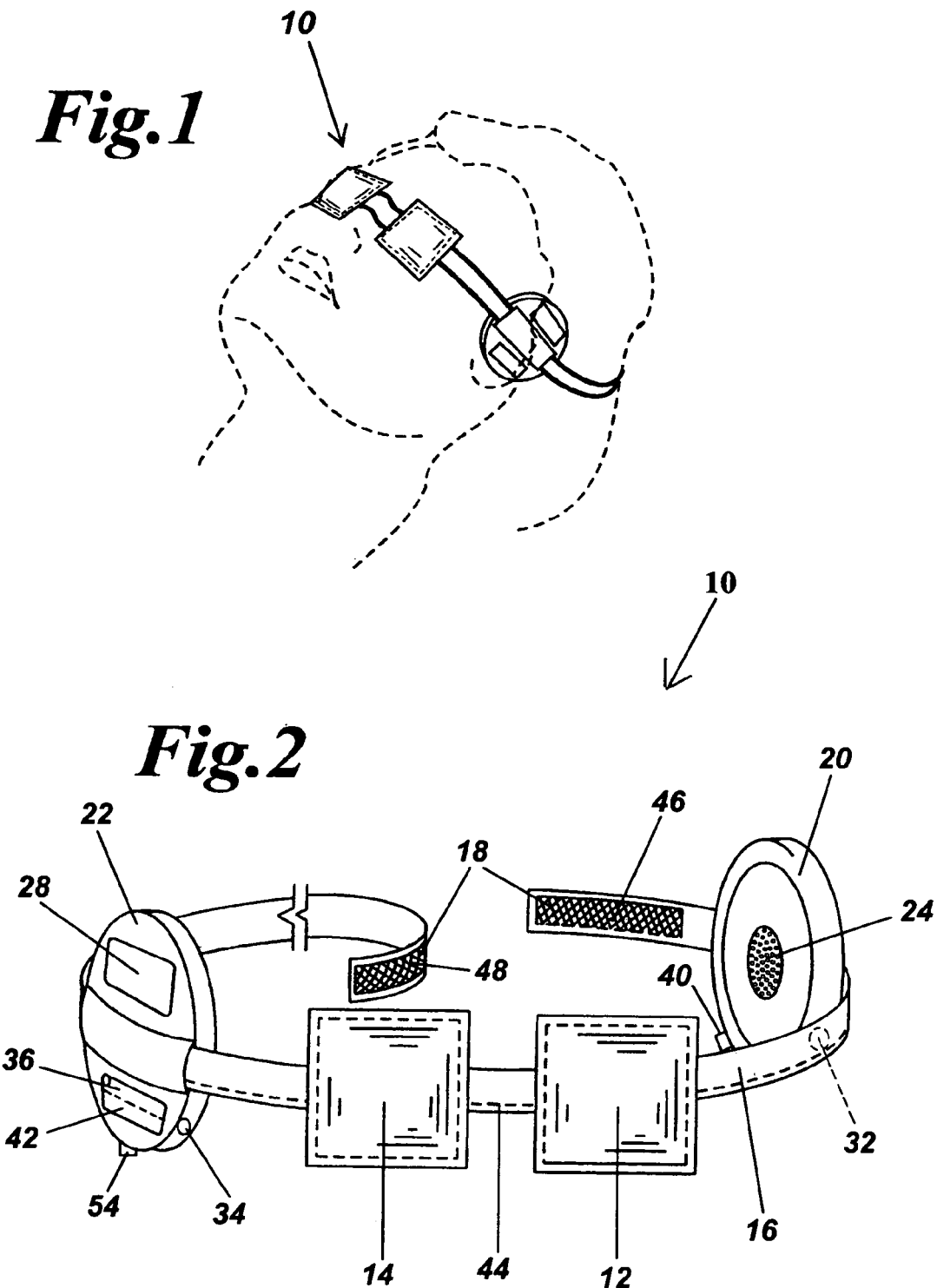

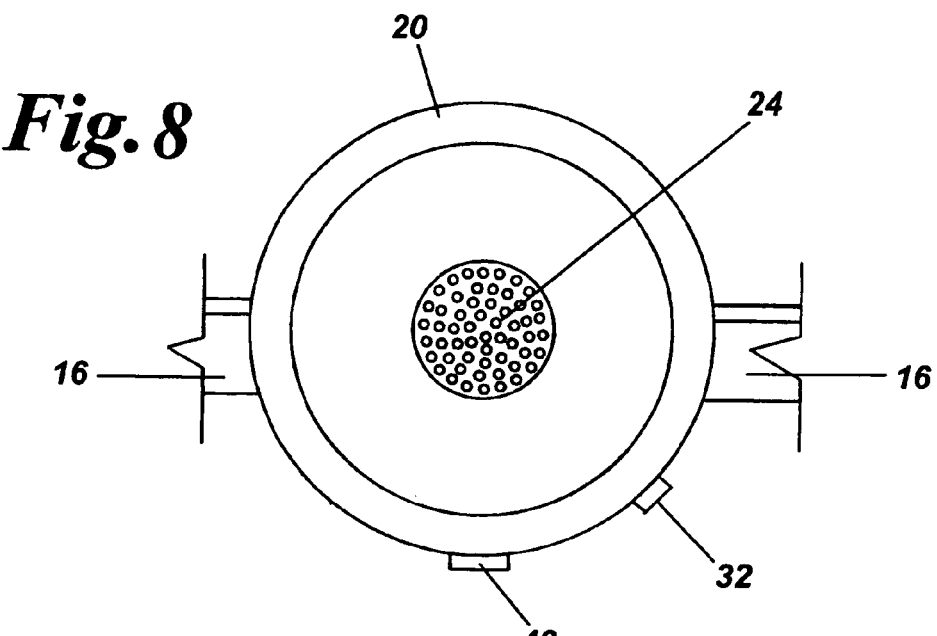
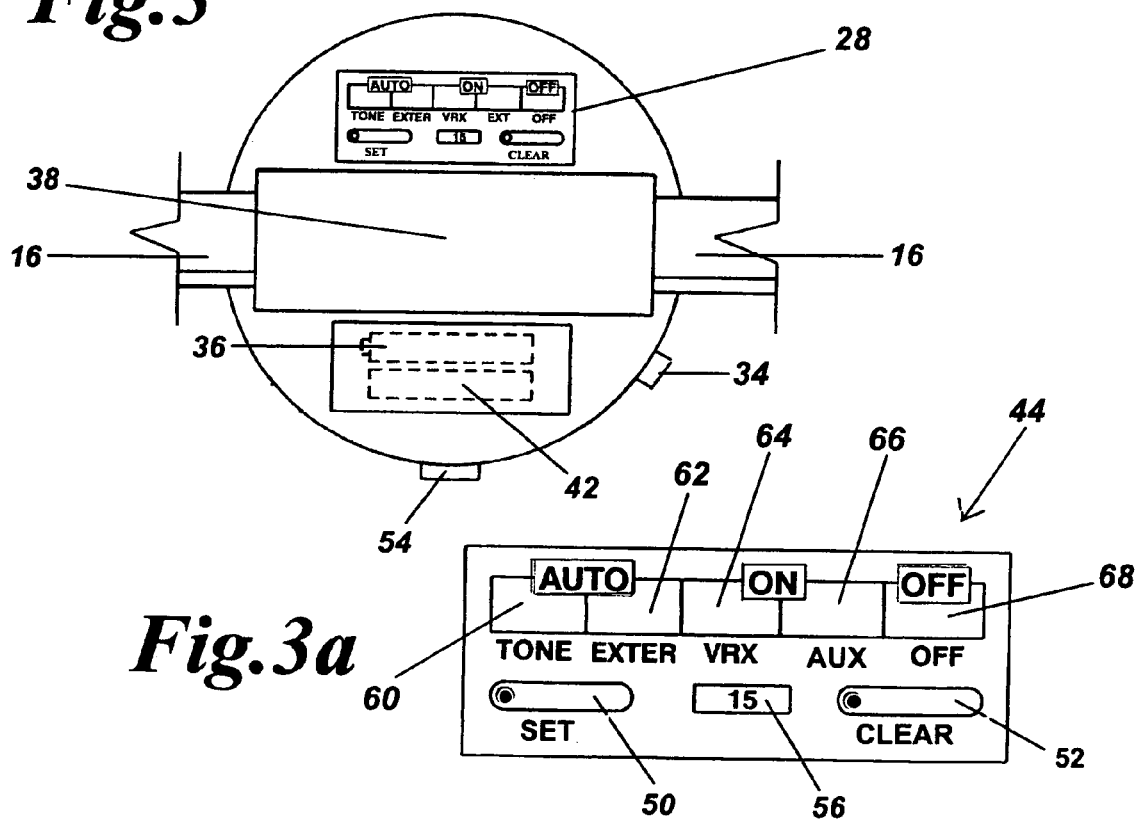

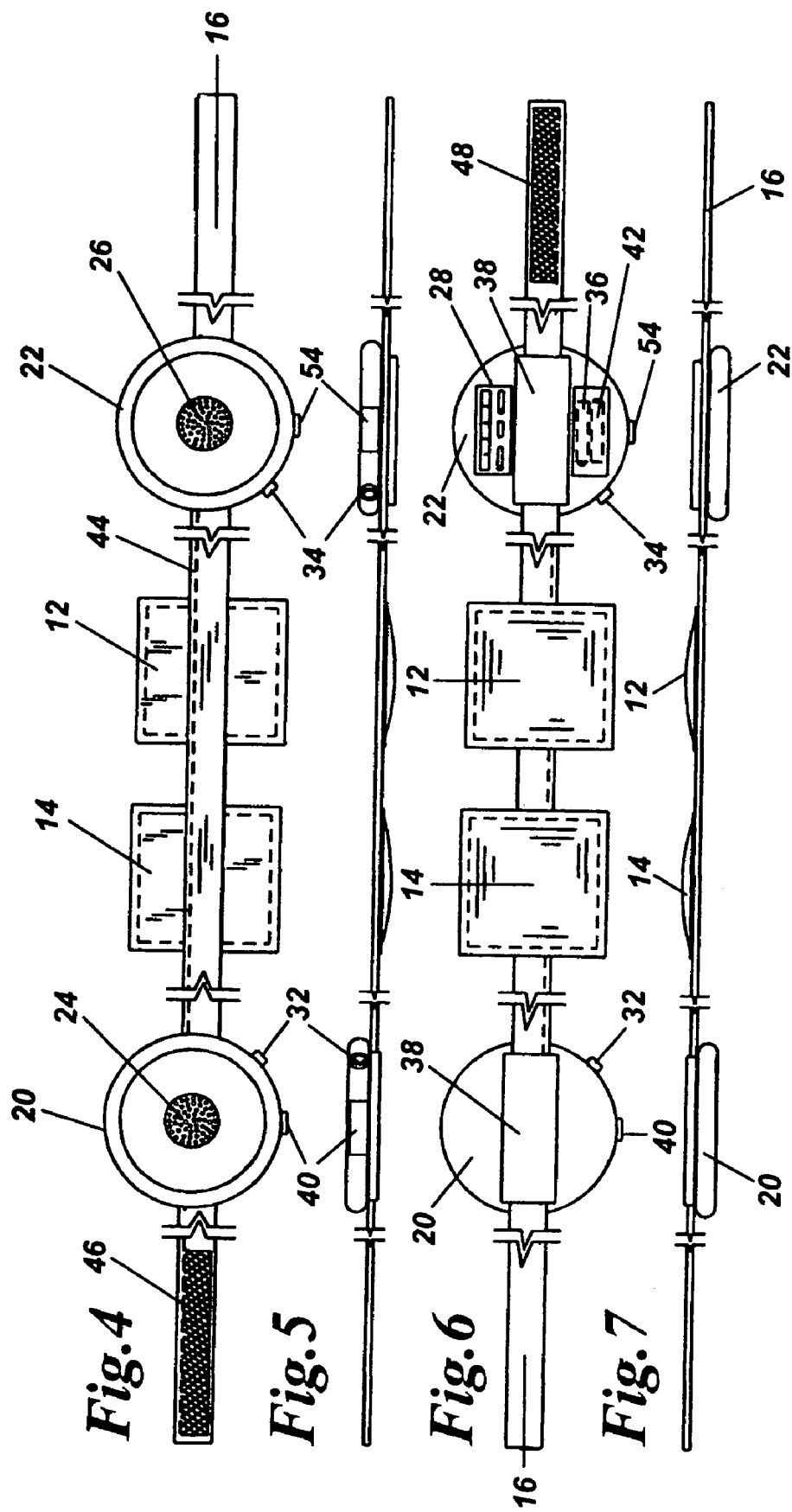

EYE SHIELD SLEEPING DEVICE

CROSS REFERENCE TO RELATED APPLICATIONS

This application is a continuation-in-part of my co-pending U.S. patent application Ser. No. 29/207,843, filed Jun. 18, 2004, which is a continuation-in-part of U.S. patent application Ser. No. 29/188,431, filed Aug. 19, 2003, now U.S. Pat. No. 492,955.

FIELD OF THE INVENTION

The present invention relates to a device and apparatus for covering the eyes of a person when desired, and more particularly to an eye shield sleeping device, where said eye shield sleeping device incorporates apparatus to augment sleeping and awakening.

BACKGROUND OF THE INVENTION

Traditional eye shields for sleeping provide an opaque mask that blocks out the ambient light, thereby creating darkness for a user, which simulates the normal nighttime conditions in which people are predisposed to sleep. In addition to darkness, an environment conducive to sleep is also typically quiet, or has a familiar background noise, such as a ticking clock, soothing music, a fan, muffled traffic noise, or the drone of a television. Ear plugs or mufflers can be incorporated into an eye shield for sleeping to attenuate the level of noise. Due to the inherent nature of light and noise, noise is more difficult to mask than light, and devices providing a means to awaken people often utilize an audio stimulating apparatus, such as an alarm buzzer or radio.

There are a number of situations where people wish to sleep, but because conditions are so disturbing that even with eye shields they are unable to sufficiently relax to fall asleep. Examples of situations that can result in sleep deprivation are athletes traveling on the road, miliary personnel in the field or in transit to a new assignment, business men and women on an extended trip, and people that are in unfamiliar sleeping quarters or in a distracting environment; for instance, traveling in a car, bus or airplane, for an extended period. In these situations, what is desired is a sleeping mask that not only screens out light, but also screens out sound. Traditional sleeping masks are relatively effective at screening out light, but tend to be less effective at screening out sound. Those sleep masks that are effective at blocking sound have the limitation that when all sound is blocked or masked, that the masks can pose as a danger, because traditional public alarm systems are audio, and cannot be heard. Therefore, it is not desired that not all sound be screened out, as it is anticipated that there will be circumstances when sounds, and especially certain alarms, words, and phrases can and should be heard. What is needed is a sleeping mask that preferably has a voice recognition system that allows alarms and designated words and phrases to be clearly audible.

Particularly in the case of athletes and military personnel, when it is often imperative that the individuals awake at a precise time in order to prepare for an event or a mission at a specified time, what is needed is a sleeping mask that has a timing means that the user can set to awaken them after an elapsed time, or at a desired time.

Many individuals have become accustomed to sleeping or being induced to a sleep state by listening to music or other background sound. A variety of synthetic mood sounds, such as the sound of moving water, wind, and birds, have been available for some time to help people sleep. In the absence of the music or the other background sounds, these individuals have a very hard time falling asleep. Therefore, what is needed is a sleeping mask that has the option of incorporating a transducer, such as head phones, to create background music or sound. To a lesser extent, other individuals have become accustomed to sleeping or being induced to a sleep state by a combination of video and audio background (i.e., television or a monitor). For these individuals, what is needed is a sleeping mask that has the option of incorporating a second type of transducer, such as a video display.

The preferred sleeping mask has multiple features for blocking out the ambient noise, generating soothing background sound, and awakening options. What is further desired is an ergonomically easy means to control these features. As previously stated, the desired sleeping mask has a voice recognition system, and what is further needed is a voice recognition system that is command driven and interactive. For example, the voice recognition system should have voice control of the volume of the transducer, so that the volume of the alarm or music can be altered. The voice recognition system should have verbal command control over the selection of the music, and the timer. What is further needed is voice activated control over an interface, where the interface may enable a cell phone to initiate a call, or to connect to a computer, an audio playing device, an audio synthesizer device, a pager, an MP3 player, or a receiver.

SUMMARY OF THE INVENTION

The invention is an eye shield sleeping device comprised of a strap, a right eye shield that is attached to the strap; a left eye shield that is attached to the strap; and a timer with one or more transducers. The timer generates a signal that is sent to the transducer(s), and the transducer(s) generates a sensory detectable output that can be used to awaken a sleeper. The transducer is typically a speaker, or a light source, or a vibrator, or a combination of the above. The eye shield sleeping device can easily be fitted onto or removed from the wearer's head. The eye shield sleeping device can be further comprised of apparatus to augment its effectiveness for creating a restful and functional environment. The device has ear covers, such as ear plugs, headphones and mufflers, to provide attenuation of the ambient sound heard by the user. The ear covers are adjustably affixed to the strap, to accommodate for the user's head. Typically, each of the ear covers are fitted with a speaker. The sensory detectable output can be a simple sound, such as a tone, or a complex sound, such as music, or a synthetic produced sound, such as flowing water, wind, waves, birds, a voiced word or expression, or a pre-recorded complex sound, or a received sound generated by an external signal source. Examples of external signal sources are electronic media and communication appliances, such as a radio, a cell phone, a computer, an MP3 player, a synthetic noise synthesizer, and a PDA. The eye shield sleeping device has an interface to receive the external signal from the external signal source. The interface can be wireless, hard wired or a coupling connection. The eye shield sleeping device can be further comprised of a voice recognition system and one or more microphones. Examples of commercially available voice recognition systems are Dragon Naturally Speaking™, IBM Via Voice™, and Prime Star™ S.O.C. (System On Chip) voice recognition chip VRX series. The voice recognition system is tailored to generate commands to control the apparatus supporting the eye shield sleeping device. The commands are issued through the microphone, and can be used to control a computer, PDA, cell phone, and the like. Preferably, the microphone(s) are located on the adjustable strap or on the ear shield. Many cell phones are available with limited voice recognition capabilities, which can complement the invented voice recognition system. The voice recognition system can, for example, be used to select the type and volume of the signal generated by the timer, set the timer, and select the external signal source. The voice recognition system can be programmed to not only recognize words and phrases, but also to recognize wake up signals, such as certain alarms, the voice of the coaches voice or the squad leader's voice, which triggers the apparatus to issue a wake up alarm.

In an alternate embodiment of the invention, the transducer generates a sensory detectable output that is visible, such as a miniature LCD screen on one or more of the eye shields. The visible sensory output can be video, and be accompanied with an audio output. A visible output has several advantages in that it is easier to mask than an audio output; allowing hearing impaired individuals can be awakened with a visible output, and a visible output is more natural in that it simulates dawn.

The eye shield sleeping device can have a self contained portable electrical power source and a means for connecting to a charging or auxiliary power supply.

The eye shields of the eye shield sleeping device are opaque, and substantially block out all ambient light. The left and right eye shields are preferably similar in shape and can be decorative. Preferred shapes are polygonal, or star shaped, or cat eyed, or elliptical, or round, or rectangular, or curvilinear.

The strap can be elastic, adjustable with opposing hook and loop fastening elements, or elastic and adjustable with a fastening means.

Anticipated applications for the invention include naps while traveling and in sleep rooms at work.

OBJECTS OF THE INVENTION

The principal object of the invention is to provide an improved eye shield sleeping device that masks sound, as well as light.

A further object of this invention is to provide a device that creates a relaxing environment that is conducive to sleeping and provides a greater degree of control over that environment.

Another object of the invention is to provide a timer for awakening the user.

Another object of the invention is to provide an eye shield sleeping device that is portable.

Another object of the invention is to provide an eye shield sleeping device that is easily adjusted to a comfortable fit on most individuals.

Another object of the invention is to provide a voice recognition system for voice control and automation of apparatus on the eye shield sleeping device.

Another object of the invention is to provide an eye shield sleeping device that can interface with multiple electronic media and communication appliances.

Another object of the invention is to provide an eye shield sleeping device that is compact and esthetically attractive, as well as functional.

BRIEF DESCRIPTION OF THE DRAWINGS

The foregoing and other objects will become more readily apparent by referring to the following detailed description and the appended drawings in which:

FIG. 1 is a perspective view of the invention, an eye shield sleeping device, as shown worn by a user. The strap is elastic, or adjustable, or elastic and adjustable.

FIG. 2 is a perspective view of the invention, an eye shield sleeping device having auxiliary apparatus to augment its effectiveness for creating a restful and functional environment.

FIG. 3 is an enlarged lateral side view of the adjustable right ear cover fitted with a timer, an interface, a voice recognition system, and a microphone.

FIG. 4 is a plan view of the inside of the eye shield sleeping device illustrating the relative position of the ear covers having speakers, and the eye shields on the adjustable strap.

FIG. 5 is a plan bottom view of the eye shield illustrating the relative position of the receptacle, the interface and the microphones.

FIG. 6 is a plan view of the outside of the eye shield sleeping device illustrating the relative position of the ear covers and the eye shields on the strap FIG. 7 is a plan top view of the eye shield illustrating the curvature of the eye shields, the thickness of ear covers, the timer and the voice recognition system.

FIG. 8 is an enlarged medial view of the left ear cover having a speaker within.

DETAILED DESCRIPTION

Referring now to the drawings, in FIG. 1, illustrates the invented eye shield sleeping device 10 as it is worn by a user. The eye shield sleeping device 10, as shown in FIG. 2, has an adjustable strap 16 with a fastening means 18. The fastening means 18 in the illustrated embodiment is an opposing pair of hook and loop fastening elements, 48 and 46, commonly known as Velcro®. Fitted to the strap 16 is a left eye shield 12 and a right eye shield 14. In the illustrated embodiment, the shields, 12 and 14, are square and slightly concave or dished out, as shown in FIG. 5 and FIG. 7. The shields are comfortable and substantially block out most of the ambient light. The eye shield sleeping device 10, as shown in FIG. 2, is further comprised of apparatus to augment relaxation and functionality. The device has a left and a right ear cover, 20 and 22, with an adjustable means 38 for positioning a cover over the ear. As shown in FIG. 2 and FIG. 3, the adjustable means 38 is substantially a sleeve through which slides the adjustable strap 16. As illustrated in FIG. 6 and FIG. 8, the medial side of each of the ear covers has an audio transducer, such as a speaker 24. The left ear cover 20 has a left speaker 24, and the right ear cover has a right speaker 26. The speakers, 24 and 26, are in electronic communication with a timer 28 through a wire 44 embedded in the strap 16, as shown in FIG. 2. The timer 28 is powered by a battery 36 as shown in FIG. 3. The timer operates similar to a clock radio, albeit with greater versatility and ergonomic considerations. Referring to FIG. 3a, the timer has an AUTO mode, an ON mode, and an OFF mode. Additionally, there is a SET mode and CLEAR mode. In the AUTO mode, the timer is activated, and the user can select an alarm source. The alarm sources are selected by a multi-position slidable switch, where position 60 selects TONE and position 62 selects EXTERNAL. The TONE source is a buzz. The EXTERNAL source enables the alarm function to turn on/input an external signal generated by devices, such as a cell phone, a radio, an MP3 player, a computer or other digital device when the timer winds down to zero minutes. In the ON mode, there are two settings, VRX and AUX. Switch position 64 selects the voice recognition system (VRX), and position 64 selects AUX, which is an external source with no alarm. When VRX is activated, control of the timer alarm and other apparatus is controlled by the voice recognition system. The user can use VRX to control the alarm with a series of verbal commands. If AUX is selected in the ON mode, then external source is selected, but with the timer 28 turned off. OFF mode has one position 68, wherein the timer and the external source are off. The SET mode, switch 50, enables the user to manually set the timer 28 in incremental minutes. The timer 28 is set using a slidably-locking SET button that in the unlocked position can be depressed, and with each depression the timer adds another increment of time to the timer. By example, when the slidably-locking set button is depressed once, five minutes are set on the timer. If the slidably-locking set button is depressed twice, then the timer is set to ten minutes before the alarm signals the user to awaken. A small LCD display 56 indicates the minutes remaining on the timer, and also serves as a means of keeping track of how much time the timer is initially set. After setting the timer, the SET button 50 is shifted sideways, thereby locking the slidably-locking set button and preventing it from being accidentally depressed as the user sleeps. The user can select the CLEAR mode using a slidably-locking clear button 52. The CLEAR mode clears the SET mode of the timer, by setting the timer to zero minutes. The slidably-locking CLEAR button 52, in effect, also acts to turn the alarm off.

Also shown, in ghost with dashed lines, in FIG. 3 is the voice recognition system 42 and the battery 36. In the illustrated embodiment the voice recognition system 42 is a system on a chip (S.O.C.) that provides a voice recognition function, and memory space for user programming inside P25K powerful DSP cornel. The battery 36 is rechargeable and can be recharged through receptacle 54, shown in FIG. 1. Both ear covers have a rechargeable battery 36, and the batteries are in electrical connection through wires, indicated by dashed line 30, that are embedded in the adjustable strap 16. The voice recognition system 42 receives verbal commands from the user through either of the two microphones, 32 and 34, mounted toward the front of ear shields, as shown in FIG. 2 and FIG. 3. The voice recognition system 42 generates confirmation and selection loops, and they are vocalized via the audio transducers, 24 and 26. In tandem, the voice recognition system and the transducers provide verbal feedback to the user, and control over the timer.

The external signal is generated by portable electronic devices selected from the group consisting of cell phones, computers, audio playing devices, audio synthesizer devices, pagers, MP3 players, and receivers. The connection as shown in FIG. 2, FIG. 3, FIG. 5 and FIG. 6 is through an interface 40, such as a jack. The interface 40 is provided on the left ear cover 20. It is anticipated that the interface can also be wireless.

Referring to FIG. 1, which illustrates how the eye shield sleeping device 10 is worn. The strap 16 is elastic and can be stretched to wrap around the user's head. The elastic strap can additionally have a fastening means that is comprised of hook 46 and loop 48 fastening elements. The fastening elements are adjusted by pressing the hook 46 against the loop 48. The ear covers 20 and 22 are adjusted to cover the user's ears, and the eye shields 14 and 16 are similarly adjusted to mask the eyes from the ambient light. The hook 46 and loop 48 fastening can then be readjusted, if necessary. The relative positions of the eye shields and the ear covers are shown in FIGS. 4–7. The ear covers are on the inside (medial side) of the strap, and have a thickness sufficient to attenuate the ambient sounds. The eye shields are slightly concave (FIGS. 5 and 7) to allow room for the user's eye lashes.

Referring to FIG. 8, which is a medial or inside view of the left ear cover 20, the ear cover 20 is comprised of a conformable sound-proofing material that fits snugly against the ear. Near the center of the ear cover, on the inside of the ear cover, is a low wattage speaker 24. The interface 40 is mounted on the outside of the ear cover 20, toward the bottom of the cover. Also mounted on the ear cover is a microphone 32, oriented forward. The microphone and speaker 24 are isolated from each other, and there is no feedback. The preferred microphone is very small, has some directionality, and is mounted slightly recessed within the ear cover.

The left and right eye shields, 12 and 14, are preferably similar in shape and are esthetically attractive. Preferred shapes are polygonal, or star shaped, or cat eyed, or elliptical, or round, or rectangular, or curvilinear.

SUMMARY OF THE ACHIEVEMENT OF THE OBJECTS OF THE INVENTION

From the foregoing, it is readily apparent that I have invented an improved eye shield sleeping device that masks sound, as well as light. The invention provides a device that creates a relaxing environment that is conducive to sleeping and provides a greater degree of control over that environment. The device is portable and provides a timer for awakening the user. The invented eye shield sleeping device is easily adjusted to a comfortable fit on most individuals. The invention provides an eye shield sleeping device that can interface with multiple electronic media and communication appliances, and a voice recognition system for voice control and automation of apparatus on the eye shield sleeping device. The resulting invention is an eye shield sleeping device that is compact and esthetically attractive, as well as functional.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is, therefore, understood to be limited only by the scope of the appended claims.

What is claimed is:

1. An eye shield sleeping device comprising:
a strap;
a right eye shield attachable to the strap;
a left eye shield attachable to the strap;
a microphone;
a voice recognition system, where said voice recognition system has a confirmation and selection loop which provides verbal feedback to a user of the eye shield sleeping device;
a timer;
a transducer;
wherein said timer activates a signal that is sent to the transducer; and
wherein said transducer generates a sensory output to the user.

2. An eye shield sleeping device according to claim 1, further comprising at least one ear cover, wherein said ear cover provides a sound barrier for the user.

3. The eye shield for sleeping, as claimed in claim 2, wherein said ear covers are adjustably affixed to the strap.

4. The eye shield sleeping device as claimed in claim 2, wherein said sensory output is audible.

5. The eye shield sleeping device as claimed in claim 2, wherein said sensory output is visible.

6. The An eye shield sleeping device according to claim 2, wherein, from a series of verbal commands by the user said voice recognition system controls a timer alarm and other apparatus.

7. An eye shield sleeping device according to claim 2, further comprising an interface for electronic communication with electronic media and communication appliances, such as a radio, a cell phone, a computer, an MP3 player, a synthetic noise synthesizer, and a PDA.

8. The eye shield sleeping device, as claimed in claim 7, wherein said interface is wireless, hard wired or quick connecting, such as with a jack.

9. The eye shield sleeping device, as claimed in claim 1, wherein said eye shield sleeping device is portable and employs a portable electrical power source.

10. An eye shield sleeping device according to claim 9, further comprising a receptacle for connecting to an electrical power source for recharging the portable electrical power source, wherein said portable power source is a battery.

11. The eye shield sleeping device as claimed in claim 1, wherein said left and right eye shields are sufficiently interiorly concave to allow for free movement of the user's eyelashes.

12. The eye shield sleeping device as claimed in claim 1, wherein said left and right eye shields are opaque, and substantially block out all ambient light.

13. The eye shield sleeping device as claimed in claim 1, wherein said left and right eye shields are similar in shape and esthetically attractive.

14. The eye shield sleeping device as claimed in claim 11, wherein said left and right eye shields are polygonal, or star shaped, or cat eyed, or elliptical, or round, or rectangular, or curvilinear.

15. The eye shield sleeping device as claimed in claim 1, wherein said strap is adjustable, wherein said fastening means is comprised of hook and loop fastening elements.

16. The eye shield sleeping device as claimed in claim 3, wherein said ear covers are comprised of a conformable sound-proofing material that fits snugly against the ear.

17. The eye shield sleeping device as claimed in claim 16, wherein the transducer is a low wattage speaker that is mounted on the inside of one or both ear covers near the center.

18. An eye shield sleeping device according to claim 2, further comprising a slidably-locking SET button for incrementally setting the time on the timer, where when said slidably-locking SET button is shifted sideways it is locked, thereby preventing it from being accidentally depressed as the user sleeps.

19. An eye shield sleeping device according to claim 2, further comprising a slidably-locking CLEAR button for resetting the timer and turning off the timer, where when said slidably-locking clear button is shifted sideways it is locked, thereby preventing it from being accidentally depressed as the user sleeps.

20. An eye shield sleeping device according to claim 2, further comprising a display, wherein said display indicates how much time remains on the timer.

21. An eye shield sleeping device comprising:
  a strap;
  a right eye shield, where said shield is attachable to the strap;
  a left eye shield is attachable to the strap;
  a timer with a speaker;
  at least one ear cover that is adjustably affixed to the strap;
  a voice recognition system, where said voice recognition system recognizes wake up signals, the voice of a coach or squad leader, and upon such recognition of the wake up signal, or the voice of a coach or squad leader, and triggers the eye shield sleeping device to issue a wake up alarm;
  a microphone;
  a battery;
  wherein said timer or voice recognition system activates a signal that is sent to the speaker; and
  wherein said speaker is mounted within the cover and generates a sound that can awaken a user.

22. The eye shield sleeping device as claimed in claim 1, wherein said sensory output emanates from apparatus selected from the group consisting of:
  a speaker, a light source, a vibrator, a video display, or a combination of two or more.

23. The eye shield sleeping device as claimed in claim 1, wherein said strap is elastic.

* * * * *